United States Patent [19]

Abrams et al.

[11] Patent Number: 5,637,089

[45] Date of Patent: Jun. 10, 1997

[54] SUPERELASTIC GUIDING MEMBER

[75] Inventors: Robert M. Abrams, Carlsbad; Sepehr Fariabi, Fremont, both of Calif.

[73] Assignee: Advanced Cardiovascular Systems, Inc., Santa Clara, Calif.

[21] Appl. No.: 598,639

[22] Filed: Feb. 12, 1996

Related U.S. Application Data

[63] Continuation of Ser. No. 527,650, Sep. 13, 1995, abandoned, which is a continuation of Ser. No. 212,431, Mar. 11, 1994, abandoned, and a continuation-in-part of Ser. No. 994,679, Dec. 22, 1992, Pat. No. 5,341,818, and Ser. No. 71,322, Jun. 2, 1993, abandoned, which is a continuation of Ser. No. 629,381, Dec. 18, 1990, abandoned.

[51] Int. Cl.⁶ ............................................. A61M 37/00
[52] U.S. Cl. ................................... 604/95; 128/772
[58] Field of Search .................................. 128/657, 712, 128/833; 604/95, 280, 283, 281, 282, 164, 170; 606/78, 60, 200, 108

[56] References Cited

U.S. PATENT DOCUMENTS

| | | | |
|---|---|---|---|
| 2,738,294 | 3/1956 | Spence | 134/42 |
| 2,768,271 | 10/1956 | Meredith | 219/85 |
| 3,558,369 | 1/1971 | Wang et al. | 148/11.5 |
| 3,605,725 | 9/1971 | Bentov | 128/205 |
| 3,620,212 | 11/1971 | Fannon et al. | 128/130 |
| 3,890,977 | 6/1975 | Wilson | 128/418 |
| 3,953,253 | 4/1976 | Clark | 148/131 |
| 4,037,324 | 7/1977 | Andreasen | 32/14 |
| 4,233,690 | 11/1980 | Akins | 3/1.5 |
| 4,283,233 | 8/1981 | Goldstein et al. | 148/11.5 |
| 4,411,655 | 10/1983 | Schreck | 604/125 |
| 4,425,908 | 1/1984 | Simon | 128/1 |
| 4,427,000 | 1/1984 | Ueda | 128/6 |
| 4,503,569 | 3/1985 | Dotter | 3/1.4 |
| 4,505,767 | 3/1985 | Quin | 420/441 |
| 4,512,338 | 4/1985 | Balko et al. | 128/1 |
| 4,533,411 | 8/1985 | Melton | 148/402 |
| 4,580,568 | 4/1986 | Gianturco | 128/345 |

(List continued on next page.)

FOREIGN PATENT DOCUMENTS

| | | | |
|---|---|---|---|
| 0 480 427 A1 | 4/1992 | European Pat. Off. | |
| 0491 349 A3 | 6/1992 | European Pat. Off. | 604/281 |
| 0 515 078 A2 | 11/1992 | European Pat. Off. | 604/281 |
| 0 550 258 A1 | 7/1993 | European Pat. Off. | |
| 0 569 166 A1 | 11/1993 | European Pat. Off. | 604/281 |
| 55-164304 | 11/1980 | Japan | |
| 60-21469 | 2/1985 | Japan | |
| 61-40410 | 2/1986 | Japan | |
| 63-68834 | 3/1988 | Japan | |
| WO 89/10088 | 2/1989 | WIPO | |
| 9013329 | 11/1990 | WIPO | 604/281 |
| WO 91/15152 | 10/1991 | WIPO | |

*Primary Examiner*—Vincent Millin
*Assistant Examiner*—N. Kent Gring
*Attorney, Agent, or Firm*—Heller Ehrman White & McAuliffe

[57] ABSTRACT

An improved guiding member for use within a body lumen having a unique combination of superelastic characteristics. The superelastic alloy material has a composition consisting of about 30% to about 52% (atomic) titanium, and about 38% to 52% nickel and may have one or more elements selected from the group consisting of iron, cobalt, platinum, palladium, vanadium, copper, zirconium, hafnium and niobium. The alloy material is subjected to thermomechanical processing which includes a final cold working of about 10 to about 75% and then a heat treatment at a temperature between about 450° and about 600° C. and preferably about 475° to about 550° C. Before the heat treatment the cold worked alloy material is preferably subjected to mechanical straightening. The alloy material is preferably subjected to stresses equal to about 5 to about 50% of the room temperature ultimate yield stress of the material during the thermal treatment. The guiding member using such improved material exhibits a stress-induced austenite-to-martensite phase transformation at an exceptionally high constant yield strength of over 90 ksi for solid members and over 70 ksi for tubular members with a broad recoverable strain of at least about 4% during the phase transformation. An essentially whip free product is obtained.

6 Claims, 3 Drawing Sheets

U.S. PATENT DOCUMENTS

| | | | |
|---|---|---|---|
| 4,665,906 | 5/1987 | Jervis | 128/92 |
| 4,768,507 | 9/1988 | Fischell et al. | 128/303 |
| 4,776,844 | 10/1988 | Ueda | 604/95 |
| 4,827,941 | 5/1989 | Taylor et al. | 128/772 |
| 4,875,489 | 10/1989 | Messner et al. | 128/657 |
| 4,881,981 | 11/1989 | Thoma et al. | 148/11.5 |
| 4,925,445 | 5/1990 | Sakamoto et al. | 604/95 |
| 4,935,068 | 6/1990 | Duerig | 148/402 |
| 4,943,326 | 7/1990 | Ozawa et al. | 148/11.5 N |
| 4,984,581 | 1/1991 | Stice | 604/95 |
| 4,991,602 | 2/1991 | Amplatz et al. | 604/164 |
| 5,025,799 | 6/1991 | Wilson | 604/95 |
| 5,067,957 | 11/1991 | Jervis | 606/78 |
| 5,069,226 | 12/1991 | Yamauchi et al. | 604/95 |
| 5,120,308 | 6/1992 | Hess | 128/772 |
| 5,143,085 | 9/1992 | Wilson | 128/772 |
| 5,188,621 | 2/1993 | Samson | 128/657 |
| 5,318,527 | 6/1994 | Hyde et al. | 604/95 |
| 5,341,818 | 8/1994 | Abrams et al. | 128/772 |

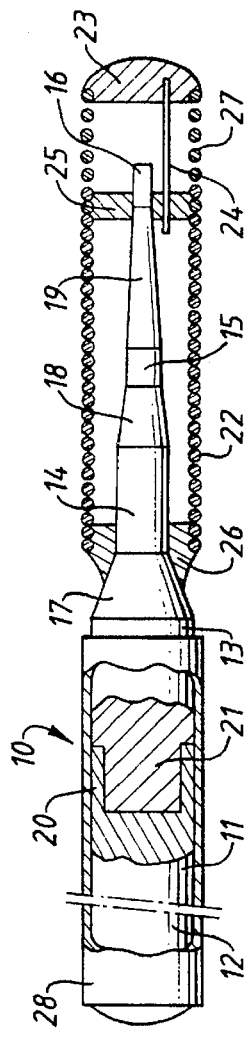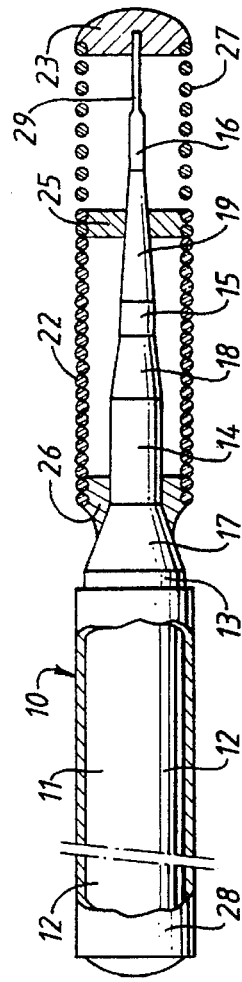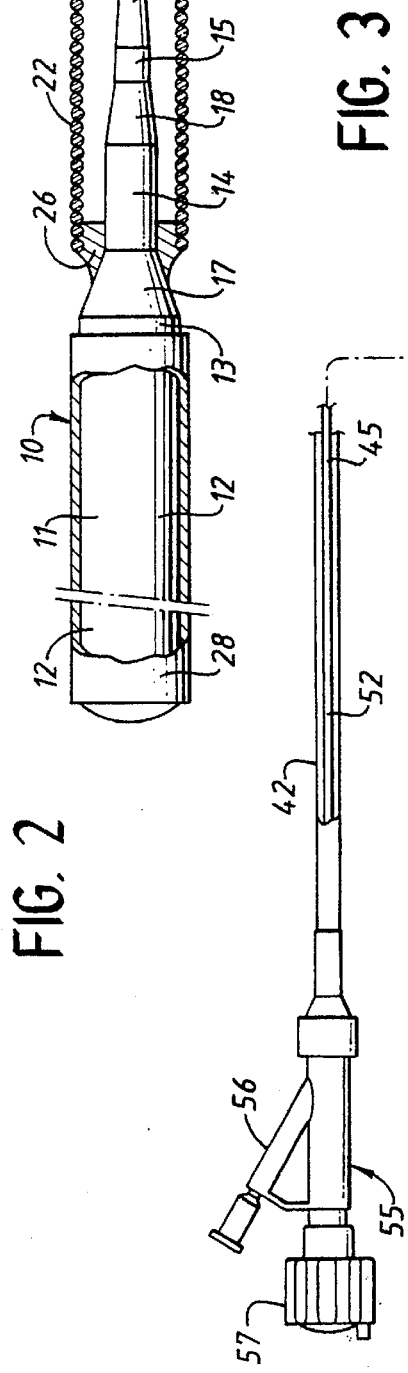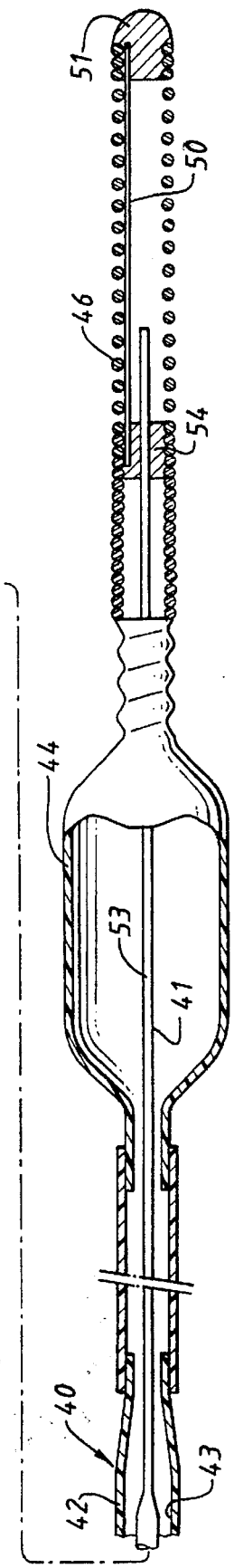
FIG. 1
FIG. 2
FIG. 3

SUPERELASTIC GUIDING MEMBER

This is a continuation of application Ser. No. 08/527,650, filed Sep. 13, 1995 now abandoned, which is a continuation of application Ser. No. 08/212,431, filed on Mar. 11, 1994 and a continuation-in-part of application Ser. No. 07/994,679, filed on Dec. 22, 1992, now U.S. Pat. No. 5,341,818, and a continuation-in-part of application Ser. No. 07/071,322, filed on Jun. 2, 1993, abandoned, which is a continuation of application Ser. No. 07/629,381, filed on Dec. 18, 1990, abandoned, for SUPERELASTIC GUIDING MEMBER.

BACKGROUND OF THE INVENTION

This invention relates to the field of medical devices, and more particularly to guiding means such as guidewires for advancing catheters within body lumens in procedures such as percutaneous transluminal coronary angioplasty (PTCA).

In typical PTCA procedures a guiding catheter having a preformed distal tip is percutaneously introduced into the cardiovascular system of a patient in a conventional Seldiger technique and advanced therein until the distal tip of the guiding catheter is seated in the ostium of a desired coronary artery. A guidewire is positioned within an inner lumen of a dilatation catheter and then both are advanced through the guiding catheter to the distal end thereof. The guidewire is first advanced out of the distal end of the guiding catheter into the patient's coronary vasculature until the distal end of the guidewire crosses a lesion to be dilated, then the dilatation catheter having an inflatable balloon on the distal portion thereof is advanced into the patient's coronary anatomy over the previously introduced guidewire until the balloon of the dilatation catheter is properly positioned across the lesion. Once in position across the lesion, the balloon is inflated to a predetermined size with radiopaque liquid at relatively high pressures (e.g. greater than 4 atmospheres) to compress the arteriosclerotic plaque of the lesion against the inside of the artery wall and to otherwise expand the inner lumen of the artery. The balloon is then deflated so that blood flow is resumed through the dilated artery and the dilatation catheter can be removed therefrom.

Conventional guidewires for angioplasty and other vascular procedures usually comprise an elongated core member with one or more tapered sections near the distal end thereof and a flexible body such as a helical coil disposed about the distal portion of the core member. A shapable member, which may be the distal extremity of the core member or a separate shaping ribbon which is secured to the distal extremity of the core member extends through the flexible body and is secured to a rounded plug at the distal end of the flexible body. Torquing means are provided on the proximal end of the core member to rotate, and thereby steer, the guidewire while it is being advanced through a patient's vascular system.

Further details of dilatation catheters, guidewires, and devices associated therewith for angioplasty procedures can be found in U.S. Pat. No. 4,323,071 (Simpson et al.); U.S. Pat. No. 4,439,185 (Lundquist); U.S. Pat. No. 4,516,972 (Samson); U.S. Pat. No. 4,538,622 (Samson et al.); U.S. Pat. No. 4,554,929 (Samson et al.); U.S. Pat. No. 4,616,652 (Simpson); and U.S. Pat. No. 4,638,805 (Powell).

Steerable dilatation catheters with fixed, built-in guiding members, such as described in U.S. Pat. No. 4,582,181 (now Re 33,166) are frequently used because they have lower deflated profiles than conventional over-the-wire dilatation catheters and a lower profile allows the catheter to cross tighter lesions and to be advanced much deeper into a patient's coronary anatomy.

A major requirement for guidewires and other guiding members, whether they be solid wire or tubular members, is that they have sufficient columnar strength to be pushed through a patient's vascular system or other body lumen without kinking. However, they must also be flexible enough to avoid damaging the blood vessel or other body lumen through which they are advanced. Efforts have been made to improve both the strength and flexibility of guidewires to make them more suitable for their intended uses, but these two properties are for the most part diametrically opposed to one another in that an increase in one usually involves a decrease in the other.

The prior art makes reference to the use of alloys such as NITINOL, which is an acronym for Ni-Ti Naval Ordnance Laboratory. These alloys have shape memory and/or superelastic characteristics and may be used in medical devices which are designed to be inserted into a patient's body. The shape memory characteristics allow the devices to be deformed to facilitate their insertion into a body lumen or cavity and then be heated within the body so that the device returns to its original shape. Superelastic characteristics on the other hand generally allow the metal to be deformed and restrained in the deformed condition to facilitate the insertion of the medical device containing the metal into a patient's body, with such deformation causing the phase transformation. Once within the body lumen the restraint on the superelastic member can be removed, thereby reducing the stress therein so that the superelastic member can return to its original undeformed shape by the transformation back to the original phase.

Alloys having shape memory/superelastic characteristics generally have at least two phases. These phases are a martensite phase, which has a relatively low tensile strength and which is stable at relatively low temperatures, and an austenite phase, which has a relatively high tensile strength and which is stable at temperatures higher than the martensite phase.

Shape memory characteristics are imparted to the alloy by heating the metal at a temperature above which the transformation from the martensite phase to the austenite phase is complete, i.e. a temperature above which the austenite phase is stable. The shape of the metal during this heat treatment is the shape "remembered". The heat treated metal is cooled to a temperature at which the martensite phase is stable, causing the austenite phase to transform to the martensite phase. The metal in the martensite phase is then plastically deformed, e.g. to facilitate the entry thereof into a patient's body. Subsequent heating of the deformed martensite phase to a temperature above the martensite to austenite transformation temperature causes the deformed martensite phase to transform to the austenite phase and during this phase transformation the metal reverts back to its original shape.

The prior methods of using the shape memory characteristics of these alloys in medical devices intended to be placed within a patient's body presented operational difficulties. For example, with shape memory alloys having a stable martensite temperature below body temperature, it was frequently difficult to maintain the temperature of the medical device containing such an alloy sufficiently below body temperature to prevent the transformation of the martensite phase to the austenite phase when the device was being inserted into a patient's body. With intravascular devices formed of shape memory alloys having martensiteto-austenite transformation temperatures well above body temperature, the devices could be introduced into a patient's body with little or no problem, but they had to be heated to the martensite-to-austenite transformation temperature which was frequently high enough to cause tissue damage and very high levels of pain.

When stress is applied to a specimen of a metal such as NITINOL exhibiting superelastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increase in stress are necessary to cause further deformation. The martensitic metal first yields elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity.

The prior art makes reference to the use of metal alloys having superelastic characteristics in medical devices which are intended to be inserted or otherwise used within a patient's body. See for example, U.S. Pat. No. 4,665,905 (Jervis) and U.S. Pat. No. 4,925,445 (Sakamoto et al.).

The Sakamoto et al. patent discloses the use of a nickel-titanium superelastic alloy in an intravascular guidewire which could be processed to develop relatively high yield strength levels. However, at the relatively high yield stress levels which cause the austenite-to-martensite phase transformation characteristic of the material, it did not have a very extensive stress-induced strain range in which the austenite transforms to martensite at relative constant stress. As a result, frequently as the guidewire was being advanced through a patient's tortuous vascular system, it would be stressed beyond the superelastic region, i.e. develop a permanent set or even kink which can result in tissue damage. This permanent deformation would generally require the removal of the guidewire and the replacement thereof with another.

Products of the Jervis patent on the other hand had extensive strain ranges, i.e. 2 to 8% strain, but the relatively constant stress level at which the austenite transformed to martensite was very low, e.g. 50 ksi.

What has been needed and heretofore unavailable is an elongated solid or tubular body for intravascular devices, such as guide wires or guiding members, which have at least a portion thereof exhibiting superelastic characteristics including an extended strain region over a relatively constant high stress level which effects the austenite transformation to martensite and still provide a one-to-one torque response. The present invention satisfies these and other needs.

SUMMARY OF THE INVENTION

The present invention is directed to an improved superelastic body which is suitable for intraluminal devices, such as guidewires or guiding members, wherein superelastic characteristics result from the stress-induced transformation of austenite to martensite.

The superelastic alloy body of the invention has a stable austenite phase which will transform to martensite phase upon the application of stress and will exhibit a recoverable strain of at least about 4% upon the stress induced transformation of the austenite phase to the martensite phase. The formation of the alloy body includes a final cold working about 10 to about 75% and then a final memory imparting heat treatment at a temperature of about 450° to about 600° C., preferably 475° to about 550° C. The cold worked, heat treated product exhibits a stress-induced phase transformation at temperatures below about 45° C. at a relatively high stress level, e.g. above about 70 ksi, (483 Mpa) preferably above about 90 ksi (620 Mpa) for solid products and about 40 ksi (276 Mpa) for hollow tubular products. The superelastic product exhibits at recoverable strain of at least 4% upon completion of the stress-induced transformation of the austenite phase to the martensite phase. The onset of the stress induced phase change from austenite to martensite, preferably begins when the specimen has been strained about 2% and extends to a strain level of about 8% at the completion of the phase change. The stress and strain referred to herein is measured by tensile testing. The stress-strain relationship determined by applying a bending moment to a cantilevered specimen is slightly different from the relationship determined by tensile testing because the stresses which occur in the specimen during bending are not as uniform as they are in tensile testing. The stress change during the phase transformation is much less than the stress either before or after the stress-induced transformation. In some instances the stress level during the phase change is almost constant.

The elongated portion of the guiding member having superelastic properties is preferably formed from an alloy consisting essentially of about 30 to about 52% titanium, about 38% to about 52% nickel and additional alloying elements in amount up to 20% for copper and up to about 10% in the case of other alloying elements. The additional alloying elements may be selected from the group consisting of up to 3% each of iron, cobalt, chromium, platinum, palladium, zirconium, hafnium and niobium and up to about 10% vanadium. At nickel levels above 52% the alloy becomes too brittle to fabricate by cold working. Metallurgically the alloy consist essentially of a predominant quantity of a NiTi intermetallic compound and small quantities of other constituents. Additionally, when nickel is in excess $Ni_3Ti$ is formed, whereas when titanium is in excess $Ti_2Ni$ is formed. As used herein, all references to percent alloy compositions are atomic percent unless otherwise noted.

To form the elongated superelastic portion of the guiding member, elongated solid rod or tubular stock of the preferred alloy material is first thermomechanically processed through a series of cold working, e.g. drawing and inter-annealing at temperatures between about 600° to about 800° C. for about 5 to about 30 minutes and is then given a final cold working, e.g. drawing, to effect a final size reduction of about 10% up to about 75% in the transverse cross section thereof. For solid products the final cold work is preferably about 30 to about 70% and for hollow tubular products the final cold work is preferably about 10% to about 40%. As used herein % cold work is the size reduction of the transverse dimension of the work piece effected by the cold working. After the final cold working, the material is given a heat treatment at a temperature of about 450° to about 600° C., preferably about 475° to about 550° C., for about 0.5 to about 60 minutes to generate the superelastic properties. To impart a straight memory, the cold worked material may be subjected to a longitudinal stress equal to about 5% to about 50%, preferably about 10% to about 30%, of the yield stress of the material (as measured at room temperature) during a heat treatment of about 450° to about 600° C. This thermomechanical processing imparts a straight "memory" to the superelastic portion and provides a relatively uniform residual stress in the material. Preferably, the final cold worked product is subjected to mechanically straightening between the final cold working and heat treating steps to provide the wire or tubular product with substantially improved, one-to-one torque response, i.e. it is substantially whip free. The alloy composition and thermal treatment are selected to provide an austenite finish transformation temperature generally about −20° to about 40° C. and usually less than body temperature (approx. 37° C.). To obtain more consistent final properties, it is preferred to fully anneal the solid rod or tubular stock prior to cold working so that the material will always have the same metallurgical structure at the start of the cold working. The pre-annealing also ensures adequate ductility for cold working. It will be appreciated by those skilled in the art that the alloy can be cold worked in a variety of ways other than drawing, such as rolling or swaging. The constant stress levels for tubular products have been found to be slightly lower than the constant stress levels for solid products due to the inability to cold work the tubular products to the extent the solid products can be cold worked. For example, solid superelastic wire material of the invention can have a relatively constant stress level above about 70 ksi, usually above about 90 ksi, whereas, hollow superelastic tubing material of the invention can have a relatively constant stress level above about 50 ksi (345 Mpa) usually above about 60 ksi (414 Mpa). The ultimate tensile strength of both forms of the material is well above 200 ksi (1380 Mpa) with an ultimate elongation at failure of about 15%.

The elongated body of the invention exhibits a stress-induced austenite-to-martensite phase transformation over a broad region of strain at very high, relatively constant stress levels. As a result a guiding member formed of this material is very flexible, it can be advanced through very tortuous passageways such as a patient's coronary vasculature with little risk that the superelastic portion of the guiding member will develop a permanent set and at the same time it will effectively transmit the torque applied thereto without causing the guiding member to whip.

These and other advantages of the invention will become more apparent from the following detailed description thereof when taken in conjunction with the following exemplary drawings.

BRIEF DESCRIPTION OF THE DRAWINGS

FIG. 1 illustrates a guidewire which embodies features of the invention.

FIG. 2 illustrates another embodiment of a guidewire of the invention.

FIG. 3 is a partial side elevational view, partially in section, of a guiding member embodying features of the invention which is incorporated into a fixed-wire dilatation catheter adapted for balloon angioplasty procedures.

DETAILED DESCRIPTION OF THE INVENTION

Figure 5:
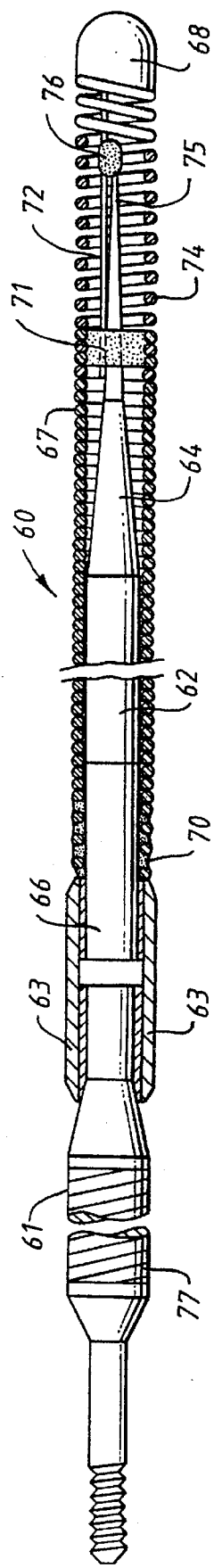
FIG. 5 illustrates another embodiment of a guidewire embodying features of the invention.

FIG. 1 illustrates a guidewire 10 embodying features of the invention that is adapted to be inserted into a body lumen such as an artery. The guidewire 10 comprises an elongated body or core member 11 having an elongated proximal portion 12 and a distal portion 13, at least part of which, preferably the distal portion, is formed of superelastic material of the invention. The distal portion 13 has a plurality of sections 14, 15 and 16 having sequentially smaller diameters with tapered sections 17, 18 and 19 connecting the smaller diameter sections with adjacent sections. The elongated proximal portion 12 is provided with a female distal end 20 which receives the male end 21 of the distal portion 13. The ends 20 and 21 may be press fit together or may be secured together by means such as a suitable adhesive or by welding, brazing or soldering.

A helical coil 22 is disposed about the distal portion 13 and has a rounded plug 23 on the distal end thereof where the distal end of the helical coil is welded to the distal end of a shaping ribbon 24 which is secured by its proximal end to the distal portion 13 by suitable means (e.g. brazing) at location 25. The coil 22 is also secured to the distal portion 13 of the elongated body 11 at location 25 and to the tapered section 17 at location 26. Preferably, the most distal section 27 of the helical coil 22 is made of radiopaque metal such as platinum or alloys thereof to facilitate the fluoroscopic observation of the distal portion of the guidewire while it is disposed within a patient's body.

The exposed portion of the elongated body 11 should be provided with a coating 28 of lubricous material such as polytetrafluoroethylene (sold under the trademark Teflon by du Pont) or other suitable lubricous coatings such as the polysiloxane coatings disclosed in co-pending application Ser. No. 559,373, filed Jul. 24, 1990 which is hereby incorporated by reference.

FIG. 2 illustrates another embodiment of a guidewire which incorporates features of the invention. This embodiment is very similar to the embodiment shown in FIG. 1 except that the entire elongated body 11 is formed of material having superelastic characteristics and the distal portion 13 of the core member 11 extends all the way to the plug 23 and is preferably flattened at its most distal extremity 29 as ribbon 24 in the embodiment shown in FIG. 1. All of the parts of the guidewire shown in FIG. 2 which correspond to the parts shown in FIG. 1 are numbered the same as in FIG. 1.

FIG. 3 illustrates a fixed wire, steerable dilatation catheter 40 which has incorporated therein a guiding member 41 in accordance with the invention. In this embodiment, the catheter 40 includes an elongated tubular member 42 having an inner lumen 43 extending therein and an inflatable, relatively inelastic dilatation balloon 44 on the distal extremity of the tubular member. Guiding member 41 which includes an elongated body 45, a helical coil 46 disposed about and secured to the distal end of the elongated body 45 and a shaping ribbon 50 extending from the distal end of the elongated body to rounded plug 51 at the distal end of the coil 46. The proximal portion 52 of the elongated body 45 is disposed within the inner lumen 43 of the tubular member 42 and the distal portion 53 of the elongated body 45 extends through the interior of the dilatation balloon 44 and out the distal end thereof. The distal end of the balloon 44 is twisted and sealed about the distal portion 53 of the elongated body 45 extending therethrough in a manner which is described in more detail in copending application Ser. No. 521,103, filed May 9, 1990, which is hereby incorporated by reference. The helical coil 46 is secured to the distal portion 53 of the elongated body 45 by suitable means such as brazing at location 54 which is the same location at which the shaping ribbon 50 is secured to the distal portion of the elongated body. Preferably, the distal portion 53 is free to rotate within the twisted seal of the distal end of the balloon 44 and means are provided to seal the distal portion 53 therein to allow air to be vented therethrough but not inflation fluid such as shown in U.S. Pat. No. 4,793,350 (Mar et al.). The proximal end of the catheter 40 is provided with a multiple arm adapter 55 which has one arm 56 for directing inflation fluid through the inner lumen 43 and the interior of the balloon 44. The proximal end of the elongated body 45 extends through the adapter 55 and is secured to the torquing handle 57 which rotates the guiding member 41 within the catheter 40 as the catheter is advanced through a patient's vascular system. The tubular member 42 may be formed of suitable plastic material such as polyethylene or polyamide or metals such as stainless steel or NITINOL. All or at least the distal portion of the tubular member 42 may be formed of the superelastic NiTi type alloy material of the invention. In an alternative construction, the elongated body 45 has a flattened distal portion which is secured to the rounded plug 51.

The elongated body 11 of the guidewire 10 and elongated body 45 of the fixed-wire catheter 40 are generally about 150 to about 200 cm (typically about 175 cm) in length with an outer diameter of about 0.01 to 0.018 inch (0.25–0.46 mm) for coronary use. Larger diameter guidewire and guiding members may be employed in peripheral arteries. The lengths of the smaller diameter sections 14, 15 and 16 can range from about 5 to about 30 cm. The tapered sections 17, 18 and 19 generally are about 3 cm in length, but these too can have various lengths depending upon the stiffness or flexibility desired in the final product. The helical coils 22 and 46 are about 20 to about 40 cm in length, have an outer diameter about the same size as the diameter of the elongated bodies 11 and 45, and are made from wire about 0.002 to 0.003 inch (0.051–0.076 mm) in diameter. The last or most distal 1.5 to about 4 cm of the coil is longitudinally expanded and preferably made of platinum or other radiopaque material to facilitate the fluoroscopic observation thereof when the guidewire or fixed wire catheter is inserted into a patient. The remaining portion of the coils 22 and 45 may be stainless steel. The transverse cross-section of the elongated bodies 11 and 45 is generally circular. However, the shaping ribbons 24 and 50 and the flattened distal section 29 have rectangular transverse cross-sections which usually have dimensions of about 0.001 by 0.003 inch (0.025–0.076 mm).

The superelastic guiding member of the invention, whether it is the entire elongated body 11 or 45 or just a portion thereof, is preferably made of an alloy material consisting essentially of about 30 to about 52% titanium, about 38 to 50% nickel and the balance one or more additional alloying elements in amounts of up to about 20%, preferably up to about 12% in the case of copper and up to 10% for other additional alloying elements. The other additional alloying elements may be selected from the group consisting of iron, cobalt, platinum, palladium, zirconium, hafnium and niobium in amounts up to 3% each and vanadium in an amount of up to 10%. The addition of nickel above equiatomic amounts with titanium and the other identified alloying elements increases the stress levels at which the stress-induced austenite-to-martensite transformation occurs and ensures that the temperature at which the martensite phase transforms to the austenite phase is well below human body temperature so that austenite is the only stable phase at body temperature. The excess nickel and additional alloying elements also help to provide an expanded strain range at very high stresses when the stress induced transformation of the austenite phase to the martensite phase occurs.

A presently preferred method for making the final configuration of the superelastic portion of the guiding member is to cold work, preferably by drawing, a rod or tubular member having a composition according to the relative proportions described above to effect a final size reduction of about 10 to about 75% and then providing a memory imparting heat treatment to the cold worked product at a temperature of about 450° to about 600° C. preferably about 475° to about 550° C., for about 0.5 to about 60 minutes. In one preferred embodiment the cold worked product is subjected to tensile stress to hold the product straight during the heat treatment to impart a straight memory thereto. In the embodiment with a solid wire product, the final cold work preferably ranges from about 30 to about 70% and the heat treatment temperature ranges from about 450° to about 600° C., preferably about 475° to about 550° C. In another presently preferred embodiment with tubular products, the final cold work ranges from about 10 to about 40% and the final memory imparting heat treatment temperature ranges are the same as mentioned above. Typical initial transverse dimensions of the rod or the tubular member prior to cold working are about 0.045 inch (1.14 mm) and about 0.25 inch (6.35 mm) respectively. If the final product is to be a tubular product, a small diameter ingot, e.g. 0.20 to about 1.5 inch (5.1–38.1 mm) in diameter and 5 to about 48 inches (12.7–122 cm) in length, may be formed into a hollow tube by extruding or by machining a longitudinal center hole through a solid rod and grinding the outer surface thereof smooth.

After each drawing step, except the last, the solid rod or tubular member is preferably annealed at a temperature of about 600° to about 800° C., typically about 675° C., for about 15 minutes in air or a protective atmosphere such as argon to relieve essentially all internal stresses. In this manner all of the specimens start the subsequent thermomechanical processing in essentially the same metallurgical condition so that consistent final properties are obtained. Such treatment also provides the requisite ductility for effective subsequent cold working. The stress relieved stock is preferably drawn through one or more dies of appropriate inner diameter with a reduction per pass of about 10 to 70%. The final heat treatment fixes the austenite-martensite transformation temperature. Mechanical straightening prior to the final heat treatment, particularly when tension is applied during the last heat treatment ensures a uniform level of residual stresses throughout the length of the superelastic material which minimizes or eliminates guidewire whipping when made of this material when torqued within a patient's blood vessel.

In a typical procedure, starting with solid rod stock 0.100 inch (2.54 mm) in diameter, the cold working/heat treatment schedule would be performed as follows:

1. Cold work 60% from 0.100 inch to 0.0632 inch (1.61 mm) and anneal at 675° C. for 15 minutes.
2. Cold work 60% form 0.0632 inch to 0.0399 inch (1.02 mm) and anneal at 675° C. for 15 minutes.
3. Cold work 60% by drawing through 2–3 dies from 0.0399 inch to 0.0252 inch (0.64 mm) and anneal at 675° C. for 15 minutes.
5. Cold work 69% by drawing through 2–3 dies from 0.0252 inch to 0.014 inch (0.36 mm).
6. Mechanically straighten and then continuously heat treat at 510° C. at 1 ft/min (0.0305 m/min) under sufficient tension to impart a straight memory.

When the cold worked material is subjected to the slightly lower thermal treatments, it has substantially higher tensile properties and it exhibits stress-induced austenite to martensite phase transformation at very high levels of stress but the stress during the phase transformation is not very constant. The addition of mechanical straightening prior to the final memory imparting heat treatment under tension will substantially improve the whipping characteristics of the final product.

Figure 4:
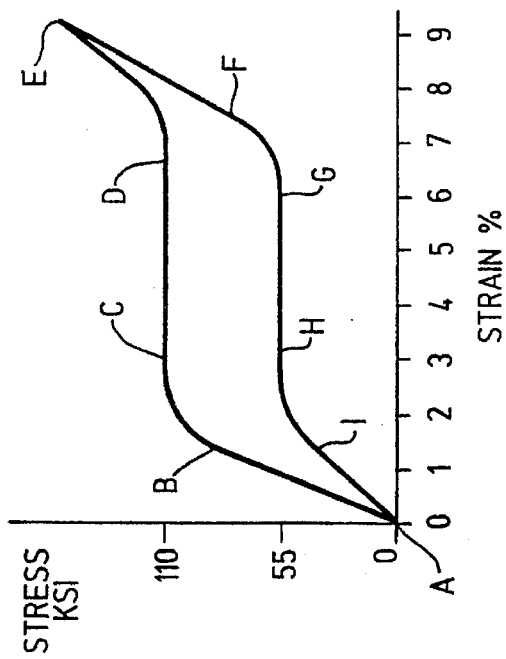
FIG. 4 is a schematic, graphical illustration of the stress-strain relationship of superelastic material.

FIG. 4 illustrates an idealized stress-strain relationship of an alloy specimen having superelastic properties as would be exhibited upon tensile testing of the specimen. The line from point A to point B thereon represents the elastic deformation of the specimen. After point B the strain or deformation is no longer proportional to the applied stress and it is in the region between point B and point C that the stress-induced transformation of the austenite phase to the martensite phase begins to occur. There can be an intermediate phase developed, sometimes called the rhombohedral phase, depending upon the composition of the alloy. At point C the material enters a region of relatively constant stress with significant deformation or strain. It is in the region of point C to point D that the transformation from austenite to martensite occurs. At point D the stress induced transformation to the martensite phase is substantially complete. Beyond point D the stress-induced martensite phase begins to deform, elastically at first, but, beyond point E, the deformation is plastic or permanent. If plastic deformation occurs, the strain will not return to zero upon the removal of the stress.

When the stress applied to the superelastic metal is removed, the metal will recover to its original shape, provided that there was no permanent deformation to the martensite phase. At point F in the recovery process, the metal begins to transform from the stress-induced, unstable martensite phase back to the more stable austenite phase. In the region from point G to point H, which is also an essentially constant stress region, the phase transformation from martensite back to austenite is essentially complete. The line from point I to the starting point A represents the elastic recovery of the metal to its original shape.

FIG. 5 illustrates a guidewire 60 embodying features of the invention which comprises an elongated, relatively high strength proximal portion 61, a relatively short distal portion 62 which is formed substantially of superelastic alloy material and a tubular connector element 63 which is formed substantially of superelastic alloy material and which connects the proximal end of the distal portion 62 to the distal end of the proximal portion 61 into a torque transmitting relationship. The distal portion 62 has at least one tapered section 64 which becomes smaller in the distal direction. The connector element 63 is a hollow tubular shaped element having an inner lumen extending therein which is adapted to receive the proximal end 65 of the distal portion 62 and the distal end 66 of the proximal portion 61. The ends 65 and 66 may be press fit into the connector element 63 or they may be secured therein by crimping or swaging the connector element or by means such as a suitable adhesive or by welding, brazing or soldering.

A helical coil 67 is disposed about the distal portion 62 and has a rounded plug 68 on the distal end thereof. The coil 67 is secured to the distal portion 62 at proximal location 70 and at intermediate location 71 by a suitable solder. A shaping ribbon 72 is secured by its proximal end to the distal portion 62 at the same location 71 by the solder and by the distal end thereof to the rounded plug 68 which is usually formed by soldering or welding the distal end of the coil 67 to the distal tip of the shaping ribbon 72. Preferably, the distal section 74 of the helical coil 67 is made of radiopaque metal such as platinum or platinum-nickel alloys to facilitate the observation thereof while it is disposed within a patient's body. The distal section 74 should be stretched about 10 to about 30%.

The most distal part 75 of the distal portion 62 is flattened into a rectangular section and preferably provided with a rounded tip 76, e.g. solder, to prevent the passage of the most distal part through the spacing between the stretched distal section 74 of the helical coil 67.

The exposed portion of the elongated proximal portion 61 should be provided with a coating 77 of lubricous material such as polytetrafluoroethylene (sold under the trademark Teflon by du Pont, de Nemours & Co.) or other suitable lubricous coatings such as the polysiloxane coatings disclosed in co-pending application Ser. No. 559,373, filed Jul. 24, 1990 which is hereby incorporated by reference.

The elongated proximal portions of the guidewires of the invention for coronary use are generally about 130 to about 140 cm in length with outer diameters of about 0.006 to 0.018 inch (0.152–0.457 mm). Larger diameter guidewires may be employed in peripheral arteries and other body lumens. The lengths of the smaller diameter and tapered sections can range from about 2 to about 20 cm, depending upon the stiffness or flexibility desired in the final product. The helical coils are about 20 to about 45 cm in length, have an outer diameter about the same size as the diameter of the elongated proximal portions, and are made from wire about 0.002 to 0.003 inch in diameter. The shaping ribbons and the flattened distal sections of the distal portions have rectangular transverse cross-sections which usually have dimensions of about 0.001 by 0.003 inch.

An important feature of the present invention is the capability of maintaining the level of the yield stress which effects the stress induced austenite-to-martensite transformation as high as possible, e.g. above 70 ksi, preferably above 90 ksi for solid products (lower with tubular products), with an extensive region of recoverable strain, e.g. a strain range of at least 4%, preferably at least 5%, which occurs during the phase transformation particularly at relatively constant stress.

Figure 6:
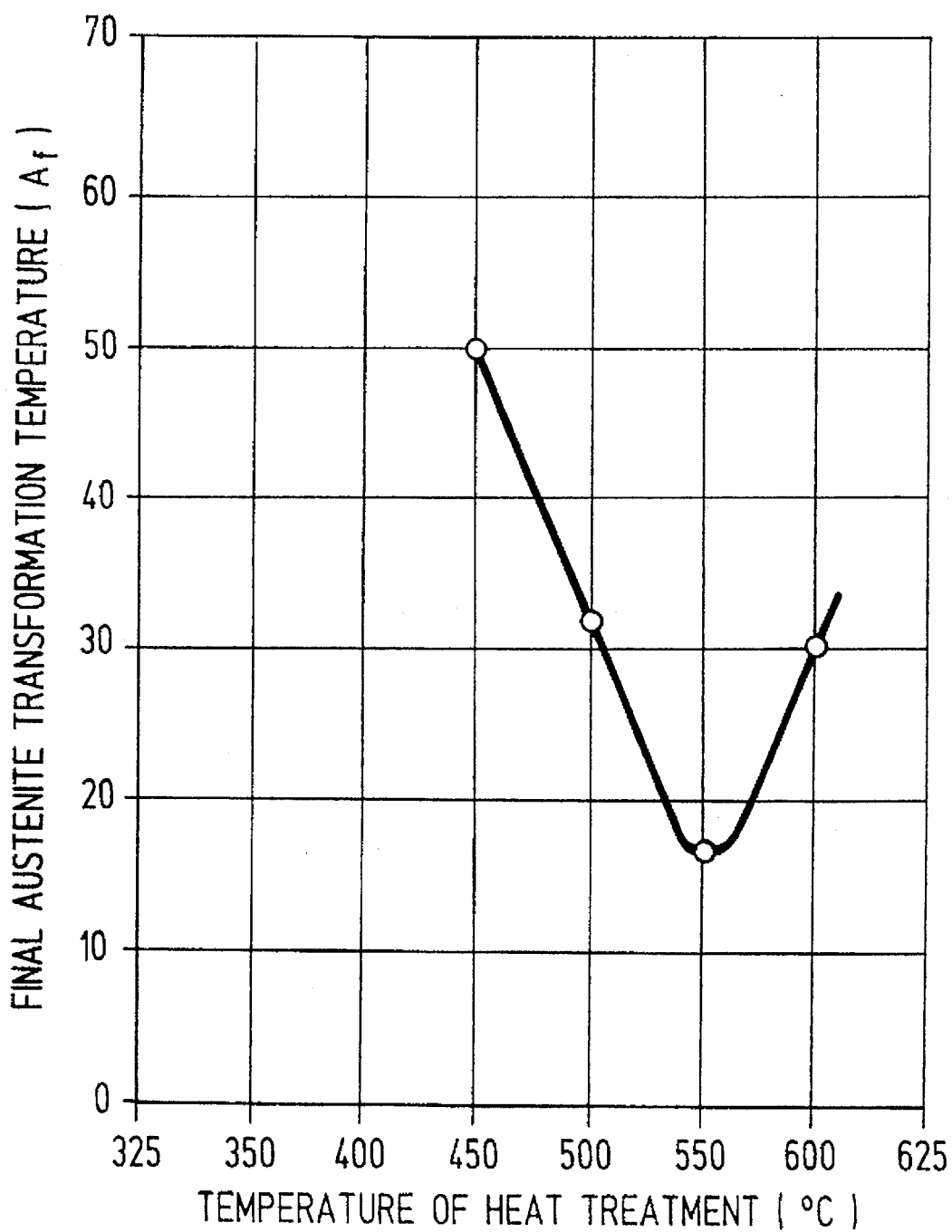
FIG. 6 illustrates the effects of the temperature during heat treatment after final cold working on the final austenite transformation temperature (Af).

FIG. 6 graphically illustrates the relationship of the final austenite transformation temperature (Af) of a binary NiTi alloy of the invention with the temperature to which the alloy is subjected during the heat treatment. The amount of cold work and composition will shift the curve to the other valves but will not change the general shape of the curve.

Because of the extended strain range under stress-induced phase transformation which is characteristic of the superelastic material described herein, a guidewire made at least in part of such material can be readily advanced through tortuous arterial passageways. When the guidewire or guiding member of the invention engages the wall of a body lumen such as a blood vessel, it will deform and in doing so will transform the austenite of the superelastic portion to martensite. Upon the disengagement of the guidewire or guiding member, the stress is reduced or eliminated from within the superelastic portion of the guidewire or guiding member and it recovers to its original shape, i.e. the shape "remembered" which is preferably straight. The straight "memory" in conjunction with little or no nonuniform residual stresses within the guidewire or guiding member prevent whipping of the guidewire when it is torqued from the proximal end thereof. Moreover, due to the very high level of stress needed to transform the austenite phase to the martensite phase, there is little chance for permanent deformation of the guidewire or the guiding member when it is advanced through a patient's artery.

The present invention provides guiding members for guidewires and fixed wire catheters which have superelastic characteristics to facilitate the advancing thereof in a body lumen. The guiding members exhibit extensive, recoverable strain resulting from stress induced phase transformation of austenite to martensite at exceptionally high stress levels which greatly minimizes the risk of damage to arteries during the advancement therein.

The superelastic tubular members of the present invention are particularly attractive for use in a wide variety of intravascular catheters, such as fixed-wire catheters wherein the Nitinol hypotubing having superelastic properties may be employed to direct inflation fluid to the interior of the dilatation balloon. In this case a guiding member may be secured to the distal end of the superelastic Nitinol tubing and extend through the interior of the inflatable balloon and out the distal end thereof. The guiding member may also be made of the superelastic Nitinol of the invention.

Superelastic hypotubing generally has been found to have a slightly lower stress level compared to wire when the austenite is transformed to martensite. However, this stress level is above 40 ksi and is usually above 70 ksi. The hypotubing of the invention generally may have an outer diameter from about 0.05 inch down to about 0.006 inch (1.27–0.152 mm) with wall thicknesses of about 0.001 to about 0.004 inch, (0.0254–0.102 mm) A presently preferred superelastic hypotubing has an outer diameter of about 0.012 inch (0.31 mm) and a wall thickness of about 0.002 inch (0.051 mm).

While the above description of the invention is directed to presently preferred embodiments, various modifications and improvements can be made to the invention without departing therefrom.

What is claimed is:

1. An intravascular guidewire comprising a) an elongated member having a proximal portion and a distal portion and being formed at least in part of a superelastic alloy consisting essentially of about 30 to about 52% titanium, about 38 to about 52% nickel and up to 20% additional alloying elements selected from the group consisting of iron, cobalt, platinum, palladium, copper and vanadium, said alloy part having an austenite phase which has a final transformation temperature below about 45° C., which transforms to a martensite phase upon the application of stress and which has been thermomechanically formed in a procedure which includes a final cold working followed by a heat treatment at a temperature between about 450° to about 600° C. while applying tension to the cold worked elongated member; and b) torquing means on the proximal portion of the elongated member.

2. The guidewire of claim 1 wherein the alloy contains one or more additional alloying elements selected from the group consisting of iron, cobalt, platinum and palladium in amounts of up to about 3%.

3. The guidewire of claim 1 wherein the alloy contains one or more additional alloying elements selected from the group consisting of copper in amounts of up to 12% and vanadium in amounts of up to about 10%.

4. The guidewire of claim 1 wherein the temperature of the heat treatment is between about 475° and about 550° C.

5. The guidewire of claim 1 wherein the superelastic part has a straight memory at a temperature less than about 45° C.

6. The guidewire of claim 1 wherein the final cold worked alloy part is mechanically straightened before the heat treatment.

* * * * *